United States Patent
Trapple

Patent Number: 5,398,341
Date of Patent: Mar. 21, 1995

[54] HINGED LENS HOLDER TRIGGERING DEVICE

[76] Inventor: James E. Trapple, P.O. Box 2507, Los Lunas, N. Mex. 87031-2507

[21] Appl. No.: 154,737

[22] Filed: Nov. 19, 1993

[51] Int. Cl.6 .............................................. A61F 9/06
[52] U.S. Cl. .................................................. 2/8; 2/9
[58] Field of Search ................. 2/7, 8, 9, 424, 410, 2/15, 10, 11, 427, 173

[56] References Cited

U.S. PATENT DOCUMENTS

| | | |
|---|---|---|
| 2,352,007 | 6/1944 | Rickert ........................................ 2/8 |
| 2,569,715 | 10/1951 | Green ......................................... 2/8 |
| 3,339,207 | 9/1967 | Perry ........................................... 2/8 |
| 3,490,071 | 1/1970 | Marshall ...................................... 2/8 |
| 3,517,392 | 6/1970 | Hodge et al. ................................ 2/8 |
| 3,601,814 | 8/1971 | Manz ........................................... 2/8 |
| 4,539,713 | 9/1985 | Hodge .......................................... 2/8 |
| 4,694,507 | 9/1987 | Owen ........................................... 2/8 |

Primary Examiner—Clifford D. Crowder
Assistant Examiner—Michael A. Neas

[57] ABSTRACT

An apparatus for closing a hinged lens holder on the front of a welding hood, without using the hands. The apparatus is a spring loaded mechanism using the chin to actuate it.

4 Claims, 1 Drawing Sheet 5,398,341

HINGED LENS HOLDER TRIGGERING DEVICE

BACKGROUND OF THE INVENTION

1. Field of the Invention

The invention relates generally to face shields, and more specifically to the welding face shields which have an eye protection lens holder in front of the eyes which is hinged and can be opened and closed by hand, while the welding face shield remains in place in front of the face. The invention is a triggering device to close the hinged lens holder using a movement of the chin to activate it.

2. Description of the Prior Art

Welding hoods are a face and eye protection shield. When in place in front of the face, they have a visual opening in front of the eyes. This opening has a lens holder, into which lenses of various shades and combinations are inserted and held in place. This lens holder is hinged on the welding hood so it can be opened and closed by hand while the welding hood remains in place. This is very advantageous as a worker may stop welding and open the hinged lens holder to inspect, chip hot slag, brush, grind, and do any number of work operations without having to remove or lift the welding hood. Also, when the hinged lens holder is open, it is customary to have a clear safety lens which remains stationary in the welding hood to protect the eyes and face during the above mentioned work operations. Thus, a welding hood with a hinged lens holder becomes a dual face and eye shield. When the hinged lens holder contains dark welding lens and is closed, it serves as a welding hood. When the hinged lens holder is open and the stationary, clear safety lens remain in place. It serves as a clear face and eye shield. The problems have been the physically removing of a hand from the work to close the hinged lens holder. Welding is a very exacting art and one hand is usually holding a tool such as an electrode and the other hand is usually in full use such as holding a work piece in place or a worker might be on a structure such as a building and using the other hand to hold on and balance. Now, when the worker is all ready to begin welding, one hand must leave the work and go up and close the hinged lens holder, then in total darkness, try to move the hand back to its position and what it was doing and also keep balance, then the worker can begin welding and see the weld by the filtered light from it. It is during this brief period of total darkness, that is repeated many times during the welding process, that balance and position are compromised, resulting in mistakes, lower quality work and it is unsafe. It is highly desirable to have the full time use of both hands. The invention allows this by using the chin and a triggering device to close the hinged lens holder instead of using a hand to close the hinged lens holder.

SUMMARY OF THE INVENTION

The invention relates to a device to close a hinged lens holder on a welding hood when a person is ready to weld. It comprises a triggering device using the chin to replace a process which previously had to be done with a hand.

It is the object of the invention to provide an inexpensive device to increase worker safety, quality, productivity, and make the work less difficult by allowing the full use of both hands for the work and using the chin as a third hand.

DESCRIPTION OF THE PREFERRED EMBODIMENT

Figure 1:
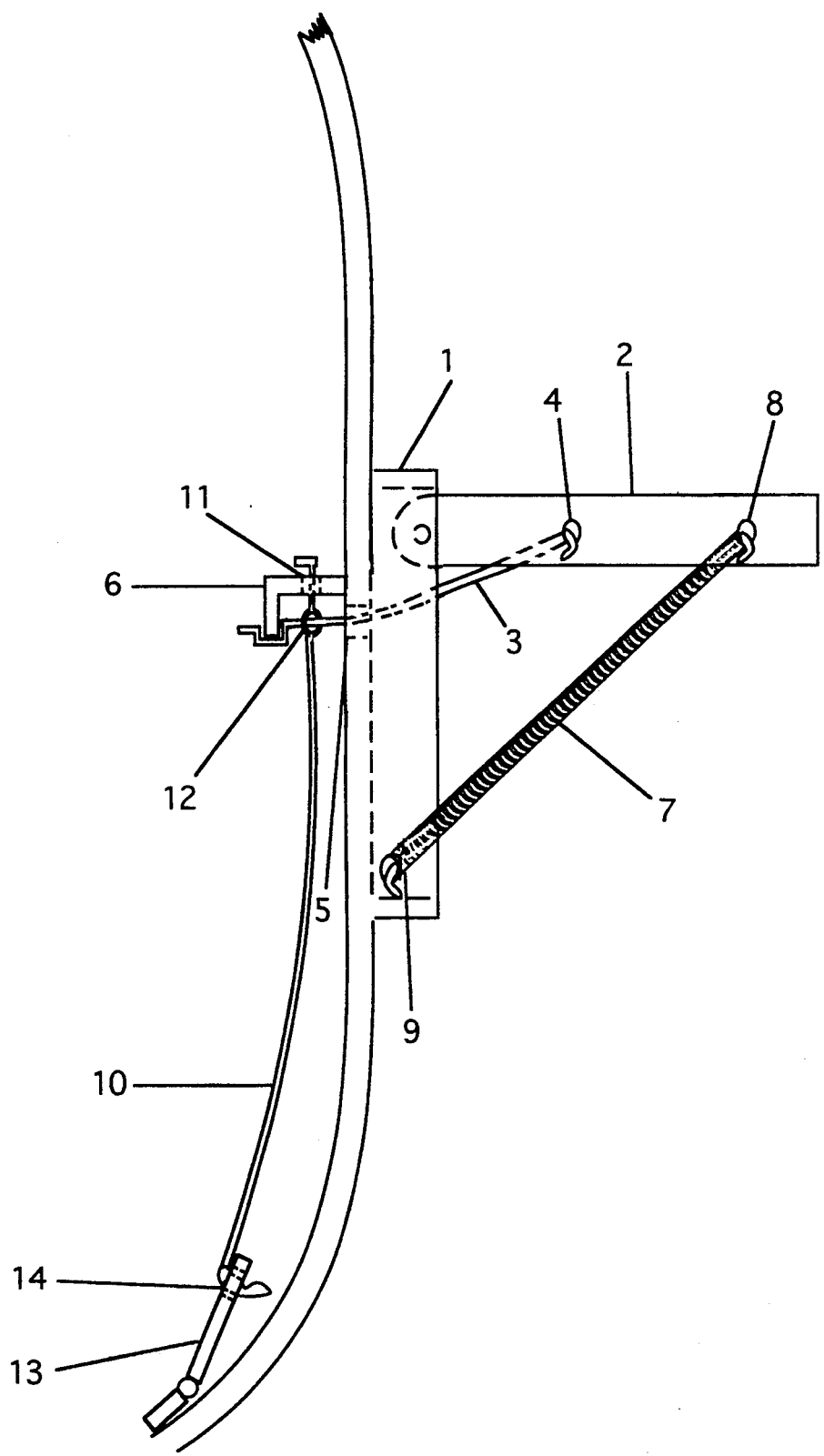
FIG. 1 is a side view of the invention.

Referring to FIG. 1, an embodiment of the invention is shown in which the Hinged Lens Holder Triggering Device is incorporated in a welding hood with a hinged lens holder. The welding hood is comprised of the entire assembly as a stationary structure 1, and the hinged lens holder as a hinged structure 2.

In this embodiment, a locking member 3, a spring wire such as a piano wire which is stiff and also flexible, is attached on one end by being hooked through a hinged structure 2, having an opening 4, then passing through a stationary structure 1, having an opening 5, which serves as a guide, then the other end being formed to fit an L shaped stop structure 6, and interlocking when in the open position as shown in FIG. 1. When opening, it uses the spring pressure of a locking member 3, against the stop structure 6, then they continue to rub together until a full open position, then the formed end of the locking member 3, snaps up against the stop structure 6, and remains in place holding the hinged structure 2, in an open position.

A spring 7, is hooked on one end through hinged structure 2, having a second opening 8, the other end is hooked through a stationary structure 1, having a second opening 9, a spring 7, is stretched and pressure applied when the hinged structure 2, is open.

An actuating member 10, on one end passes through a stop structure 6, having an opening 11, which serves as a guide, and is formed in a circle shape 12, and encircles the locking member 3.

A second hinge 13, being attached to a stationary structure 1, and having an opening 14, through which one end of an actuating member 10, may pass and hook as a means of attachment and thereby attaching actuating member 10, to a stationary structure 1.

A slight pressure of the chin against a second hinge 13, causes the actuating member 10, to move in a downward motion thereby causing the circle shape 12, to apply pressure in a downward motion against a locking member 3, thereby causing a locking member 3, to unlock from stop structure 6, thereby causing the stretched and applied pressure of a spring 7, to be activated causing a hinged structure 2, to swing in a downward motion until it comes to a stop and is closed.

Although the invention has been described in its preferred form, it is contemplated that variations in parts, materials, and positions may be resorted to in the details of construction and that in a different embodiment, the stop structure could be moved and the actuating member eliminated and the locking member would be continuous down to a position whereby a second hinge, no longer being attached, could unlock the locking member and that by reversing certain parts, the invention would open, and a voice or electrical actuating means could be used without departing from the spirit and scope of the invention as claimed.

I claim:

1. A welding hood comprising a stationary structure having a visual opening on the front thereof, a hinged structure and a device for closing said hinged structure over said visual opening, said device for closing comprising:
- (a) a means of resistance against a manual force used to open said hinged structure; and
- (b) a means to set and lock in reserve said means of resistance when said hinged structure is in an open position thereby transferring said manual force into an applied pressure; and
- (c) a means to trigger and release said applied pressure thereby propelling said hinged structure to a closed position;
- (d) said means of resistance comprising a spring having a one end and an other end, said one end attached to said stationary structure having an opening through which said one end may pass and hook and said other end attached to said hinged structure having an opening through which said other end may pass and hook;
- (e) said means to set and lock in reserve comprising a locking member having an outside end and an inside end, said outside end attached to said hinged structure having a second opening through which said outside end may pass and hook and said stationary structure having a second opening which serves as a guide for said locking member passing through to the inside of said stationary structure and said inside of said stationary structure having a formed stop structure and said inside end of said locking member formed to fit said formed stop structure and when said hinged structure is fully opened said locking member locks on to said formed stop structure;
- (f) said means to trigger and release comprising an actuating member which unlocks said locking member from said formed stop structure and said formed stop structure having an opening to serve as a guide for said actuating member wherein a slight chin pressure against said actuating member is used to trigger said device.

2. The device as recited in claim 1 in which said actuating member comprises:
a top end and a bottom end, said bottom end attached to said stationary structure and having said top end formed to contact said locking member to unlock said locking member from said formed stop structure.

3. The device as recited in claim 2, further comprising:
- (a) a second hinge attached to said stationary structure.

4. The device as recited in claim 3, further comprising:
- (a) said second hinge having an opening through which said bottom end of said actuating member may pass and hook; and
- (b) said second hinge being a means for attaching said bottom end of said actuating member to said stationary structure.

* * * * *